(12) United States Patent
Shudo et al.

(10) Patent No.: US 7,902,260 B2
(45) Date of Patent: Mar. 8, 2011

(54) MEDICAMENT FOR PREVENTIVE AND/OR THERAPEUTIC TREATMENT OF LOWER URINARY TRACT SYMPTOM

(75) Inventors: Koichi Shudo, Tokyo (JP); Tetsuji Asao, Tokorozawa (JP); Miwako Ishido, Tokyo (JP)

(73) Assignee: Kemphys Ltd., Tokyo (JP)

( * ) Notice: Subject to any disclaimer, the term of this patent is extended or adjusted under 35 U.S.C. 154(b) by 498 days.

(21) Appl. No.: 11/693,082

(22) Filed: Mar. 29, 2007

(65) Prior Publication Data
US 2008/0207768 A1    Aug. 28, 2008

(30) Foreign Application Priority Data
Feb. 28, 2007   (JP) .................. 2007-048524

(51) Int. Cl.
| | |
|---|---|
| A01N 31/04 | (2006.01) |
| A01N 37/18 | (2006.01) |
| A01N 37/12 | (2006.01) |
| A01N 37/44 | (2006.01) |
| A61K 31/195 | (2006.01) |
| A61K 31/07 | (2006.01) |
| A61K 31/16 | (2006.01) |

(52) U.S. Cl. .................. 514/725; 514/613; 514/563
(58) Field of Classification Search .................. 514/725, 514/613, 563
See application file for complete search history.

(56) References Cited

U.S. PATENT DOCUMENTS

| | | | |
|---|---|---|---|
| 4,703,110 A | 10/1987 | Shudo | |
| 5,733,721 A * | 3/1998 | Hemstreet et al. | 435/6 |
| 5,929,069 A | 7/1999 | Shudo | |
| 6,329,428 B1 * | 12/2001 | Yamauchi et al. | 514/538 |
| 2008/0021108 A1 | 1/2008 | Shudo et al. | |

FOREIGN PATENT DOCUMENTS

| | | |
|---|---|---|
| JP | 61-022047 | 1/1986 |
| JP | 61-076440 | 4/1986 |
| JP | 10-059951 | 3/1998 |
| WO | 01/17480 A2 | 3/2001 |
| WO | 03/024394 A2 | 3/2003 |

OTHER PUBLICATIONS

Webster Ninth Dictionary, 2000. Defintion of the term "to prevent"., p. 1.*
Oikawa et al. European Journal of Pharmacology, Nov. 1993, vol. 249, Issues 1-2, pp. 113-116.*
H. Kagechika et al., J. Med. Chem., 1988, vol. 31, pp. 2182-2192.
R.M. Evans, Science, 1988, vol. 240, pp. 889-895.
M. Petkovich et al., Nature, 1987, vol. 330, pp. 444-450.
D.J. Mangelsdorf et al., Nature, 1990, vol. 345, pp. 224-229.
Y. Hashimoto, Cell Structure and Function, 1991, vol. 16, pp. 113-123.
Y. Hashimoto et al., Biochem. Biophys. Res. Commun., 1990, vol. 166, No. 3, pp. 1300-1307.
S. Rohrmann et al., Urology, 2004, vol. 64, No. 3, pp. 504-509.
H. de The at al., in: Retinoids: 10 Years on. Ed. J.H. Saurat, Basel Kager, 1991, pp. 2-9.
T. Yamakawa et al., J. Med. Chem., 1990, vol. 33, pp. 1430-1437.
U.S. Appl. No. 11/670,126 to Shudo et al., filed Feb. 1, 2007.
U.S. Appl. No. 11/854,697 to Shudo et al., filed Sep. 12, 2007.
English language Abstract of JP 61-022047, Jan. 30, 1986.
English language Abstract of JP 61-076440, Apr. 18, 1986.
English language Abstract of JP 10-059951, Mar. 3, 1998.
"Hinyokika Ryoki ni Okeru Soyaku: Ensan Tamsulosin Oyobi Ensan Solifenancin", Nippon Yakuri Gakkaishi, vol. 126, pp. 341-345, 2005.
Kawabe Kazuki, "Latest Frontiers in Pharmacotherapy for Benign Prostatic Hyperplasia", Yakugaku Zasshi, vol. 126, pp. 199-206, 2006.
International Search Report issued in connection with PCT/JP2008/000377, mailed May 27, 2008.
International Preliminary Report on Patentability issued in connection with PCT/JP2008/000377, mailed Sep. 11, 2009.
Zou et al., "Identification of Effective Retinoids for Inhibiting Growth and Inducing Apoptosis in Bladder Cancer Cells", The Journal of Urology, vol. 165, No. 3, pp. 986-992, 2001.
Yilmaz et al., "Adjuvant Effect of Vitamin A on Recurrent Lower Urinary Tract Infections" Pediatrics International, vol. 49, No. 3, pp. 310-313, 2007.
Tamibarotene AM 80, Retinobenzoic Acid, Tamibaro Drugs in R & D, vol. 5, No. 6, pp. 359-362, 2004.
Harris et al., "Potential Therapeutic Effect of All-Trans-Retinoic Acid for Interstitial Cystitis" Journal of Urology, vol. 181, No. 4, pp. 21-22, 2009.
Extended European Search Report issued in connection with EP08720291.7, dated Feb. 4, 2010.
"Hinyokika Ryoki ni Okeru Soyaku: Ensan Tamsulosin Oyobi Ensan Solifenancin", Nippon Yakuri Gakkaishi, vol. 126, pp. 341-345, 2005.

* cited by examiner

*Primary Examiner* — Sreeni Padmanabhan
*Assistant Examiner* — Samira Jean-Louis
(74) *Attorney, Agent, or Firm* — Greenblum & Bernstein, P.L.C.

(57) ABSTRACT

A medicament for preventive and/or therapeutic treatment of a lower urinary tract symptom caused by a lower urinary tract disorder, which comprises as an active ingredient a retinoid such as, for example, 4-[(5,6,7,8-tetrahydro-5,5,8,8-tetramethyl-2 -naphthalenyl)carbamoyl]benzoic acid.

2 Claims, No Drawings

MEDICAMENT FOR PREVENTIVE AND/OR THERAPEUTIC TREATMENT OF LOWER URINARY TRACT SYMPTOM

TECHNICAL FIELD

The present invention relates to a medicament for preventive and/or therapeutic treatment of lower urinary tract symptoms.

BACKGROUND ART

Lower urinary tract disorder is a general term referring to disorders of lower urinary tract functions. Lower urinary tract symptoms caused by lower urinary tract disorders are mainly classified into three groups, i.e., storage symptoms such as pollakisuria and urinary urgency, voiding symptoms such as slow stream and splitting of the urine stream, and post micturition symptoms such as feeling of incomplete emptying and post micturition dribble. Lower urinary tract symptoms also include lower urinary tract pain such as painful urination, bladder pain, and urethral pain, detrusor overactivity, and voiding difficulty. Hematuria is sometimes observed with lower urinary tract disorders. Diseases which are causes of the lower urinary tract disorders include hyperplasia of prostate, prostatitis, prostatodynia, bladder neck sclerosis, overactive bladder, interstitial cystitis, and painful bladder syndrome.

Among the aforementioned diseases, interstitial cystitis is an intractable disease whose symptoms include pollakisuria, increased desire to urinate, urinary urgency, bladder discomfort and bladder pain, in the absence of urinary tract infection or other obvious pathologic condition. Causes of interstitial cystitis have been considered to be mast cell activation, a defect of glycosaminoglycan layer, inhibition of cell proliferation at the urinary tract epithelium, autoimmune, neurogenic inflammation, nitric oxide metabolism, toxic materials, hypoxia and the like, but an apparent cause has not yet been elucidated. Although interstitial cystitis is sometimes accompanied with non-specific chronic inflammation of the bladder, anti-inflammatory drugs such as steroids are not effective for said disease or animal models of the disease. Therefore, it is considered that inflammation itself does not cause interstitial cystitis symptoms such as pollakisuria. As drug therapies for interstitial cystitis, antihistaminic drug, antidepressants, cimetidine, antibiotics, steroids, pentosan polysulfate and the like have been used. However, none of these drugs provides an effective therapeutic method, and therefore, development of a medicament that can achieve high therapeutic effectiveness has been strongly desired.

Retinoic acid (vitamin A acid), an active metabolite of vitamin A, has extremely important physiological functions, e.g., inducing differentiation of immature cells under development processes toward mature cells having specific functions, enhancement of cell proliferation, and life support action. It has been revealed that various vitamin A derivatives synthesized so far also have similar physiological functions, for example, the benzoic acid derivatives disclosed in Japanese Patent Unexamined Publication (KOKAI) Nos. (Sho) 61-22047/1986 and (Sho)61-76440/1986, and the compounds described in Journal of Medicinal Chemistry, 1988, Vol. 31, No. 11, p. 2182. "Retinoids" is a general term for retinoic acid and the aforementioned compounds having retinoic acid-like biological activities.

For example, it was proved that all-trans retinoic acid binds as a ligand to the retinoic acid receptor (RAR) present in cellular nucleus, which belongs to the intranuclear receptor super family (Evans, R. M., Science, 240, p. 889, 1988), and regulates proliferation and differentiation of animal cells or cellular mortalities through induction of the activity as a transcription factor (Petkovich, M., et al., Nature, 330, pp. 444-450, 1987). In addition, the existence of retinoid X receptor (RXR) has been elucidated whose ligand is 9-cis-retinoic acid. The retinoid X receptor has been revealed to participate in the expression of the activities of the retinoic acid by inducing or suppressing the transcription of a target gene by forming a homo-dimer or a heterodimer between the retinoic acid receptor (Mangelsdorf, D. J. et al., Nature, 345, pp. 224-229).

It has also been suggested that the aforementioned compounds having the retinoic acid-like biological activities, e.g., 4-[(5,6,7,8-tetrahydro-5,5,8,8-tetramethyl-2-naphthalenyl) carbamoyl]benzoic acid: Am80, also bind to RAR in similar manners to retinoic acid to exhibit their physiological actions (see, Hashimoto, Y., Cell Struct. Funct., 16, pp. 113-123, 1991; Hashimoto, Y., et al., Biochem. Biophys. Res. Commun., 166, pp. 1300-1307, 1990). Experimentally by using animals and clinically, these compounds were found to be useful for therapeutic and preventive treatments of vitamin A deficiency disease, hyperkeratosis of epithelial tissue, rheumatism, delayed allergy, bone diseases, leukemia and certain types of cancer.

As for relation of retinoids and lower urinary tract disorders, it was reported that no correlation was observed between lower urinary tract symptoms and blood concentration of Vitamin A (Urology, 64, pp. 504-509, 2004), and a therapeutic effect of retinoids on lower urinary tract disorders has not been reported so far.

Patent Document 1 Japanese Patent Unexamined Publication (KOKAI) No. (Sho) 61-22047
Patent Document 2 Japanese Patent Unexamined Publication (KOKAI) No. (Sho) 61-76440
Non-patent Document 1 Journal of Medicinal Chemistry, 31, No. 11, p. 2182, 1988
Non-patent Document 2 Cell Struct. Funct., 16, pp. 113-123, 1991
Non-patent Document 3 Biochem. Biophys. Res. Commun., 166, pp. 1300-1307, 1990
Non-patent Document 4 Urology, 64, pp. 504-509, 2004

DISCLOSURE OF THE INVENTION

Object to be Achieved by the Invention

An object of the present invention is to provide a medicament that is capable of exhibiting high effectiveness against lower urinary tract symptoms caused by lower urinary tract disorders. In particular, the object of the present invention is to provide a medicament that can achieve excellent preventive and/or therapeutic effect against lower urinary tract symptoms caused by lower urinary tract disorders such as interstitial cystitis and bladder pain syndrome.

Means to Achieve the Object

The inventors of the present invention conducted various researches to achieve the foregoing object. As a result, they found that retinoids such as retinoic acid had excellent preventive and/or therapeutic effects against lower urinary tract symptoms caused by lower urinary tract disorders including interstitial cystitis, bladder pain syndrome, and overactive bladder, and thus achieved the present invention.

According to the present invention, provided is a medicament for preventive and/or therapeutic treatment of a lower urinary tract symptom caused by a lower urinary tract disorder, which comprises a retinoid as an active ingredient.

According to preferred embodiments of the above invention, provided are the aforementioned medicament, wherein the lower urinary tract symptom caused by the lower urinary tract disorder is one or more symptoms selected from the group consisting of pollakisuria, urinary urgency, urinary incontinence, enuresis, abnormal bladder sensation, painful urination, bladder pain, suprapubic pain, blood in the urine, bladder discomfort, bladder pain during urinary storage, and bladder discomfort during urinary storage; the aforementioned medicament, wherein the lower urinary tract symptom caused by the lower urinary tract disorder is one or more lower urinary tract symptoms selected from the group consisting of pollakisuria, urinary incontinence, enuresis, and urinary urgency; the aforementioned medicament, wherein the lower urinary tract disorder is prostatitis, hyperplasia of prostate, prostatodynia, prostatocystitis, abscess of prostate, congestion and haemorrhage of prostate, or atrophy of prostate; the aforementioned medicament, wherein the lower urinary tract disorder is urethritis, urethral abscess, urethral stricture such as post-traumatic urethral stricture and postinfective urethral stricture, urethral fistula, urethral diverticulum, or urethral caruncle; the aforementioned medicament, wherein the lower urinary tract disorder is a pathological lesion of bladder; the aforementioned medicament, wherein the lower urinary tract disorder is bladder neck sclerosis, bladder neck obstruction, vesicointestinal fistula, diverticulum of bladder, or bladder cancer; the aforementioned medicament, wherein the lower urinary tract disorder is acute cystitis, chronic cystitis, interstitial cystitis, trigonitis, irradiation cystitis, cystitis from cancer chemotherapy agents, or tuberculous cystitis; the aforementioned medicament, wherein the lower urinary tract disorder is overactive bladder; and the aforementioned medicament wherein the lower urinary tract disorder is interstitial cystitis, or painful bladder syndrome.

According to further preferred embodiments of the above invention, provided are the aforementioned medicament, wherein the retinoid is non-natural retinoid; and the aforementioned medicament, wherein the retinoid has a basic skeleton comprising an aromatic ring bound with an aromatic carboxylic acid or tropolone by means of a bridging group.

According to still further preferred embodiments of the above invention, provided are the aforementioned medicament, wherein the retinoid is capable of binding to retinoic acid receptor (RAR) subtype α and subtype β; the aforementioned medicament, wherein the retinoid is capable of binding to retinoid X receptor X (RXR); the aforementioned medicament, wherein the retinoid is a natural retinoid or an ester thereof such as all-trans-retinoic acid, 9-cis-retinoic acid, and 13-cis-retinoic acid; the aforementioned medicament, wherein the retinoid is acitretin or an ester thereof, the aforementioned medicament, wherein the retinoid is acyclic retinoid as being polyprenoic acid including NIK-333 as a typical example; the aforementioned medicament, wherein the retinoid has a basic skeleton comprising a substituted phenyl group bound with benzoic acid or tropolone by means of a bridging group; the aforementioned medicament, wherein the retinoid is 4-[(5,6,7,8-tetrahydro-5,5,8,8-tetramethyl-2-naphthalenyl)carbamoyl]benzoic acid or 4-[(3,5-bis-trimethylsilyl-phenyl)carboxamido]benzoic acid or an ester thereof; the aforementioned medicament, wherein the retinoid comprises dibenzo[b,f][1,4]thiazepinylbenzoic acid as a basic skeleton; the aforementioned medicament, wherein the retinoid is 4-[2,3-(2,5-dimethyl-2,5-hexano)dibenzo[b,f][1,4]-thiazepin-11-yl]benzoic acid or an ester thereof, and the aforementioned medicament, wherein the retinoid is 4-[5-(4,7-dimethylbenzofuran-2-yl)pyrrol-2-yl]benzoic acid or an ester thereof.

From another aspect, provided are use of the above retinoid for manufacture of the aforementioned medicament; and a method for preventive and/or therapeutic treatment of a lower urinary tract symptom caused by a lower urinary tract disorder comprising the step of administering an effective amount of the above retinoid to a mammal including a human.

EFFECT OF THE INVENTION

The medicament of the present invention can exhibit excellent preventive and/or therapeutic effect against urinary tract symptoms caused by lower urinary tract disorders, and can reduce or eliminate various lower urinary tract symptoms such as pollakisuria, urinary urgency, urinary incontinence, enuresis, abnormal bladder sensation, painful urination, bladder pain, suprapubic pain, blood in the urine, bladder discomfort, bladder pain during urinary storage, or bladder pain during urinary storage.

BEST MODE FOR CARRYING OUT THE INVENTION

In the specification, the term "retinoid" means compounds that bind to receptors required for all trans-retinoic acid and 9-cis-retinoic acid to exhibit physiological functions thereof, and thereby exhibit actions similar to those of retinoic acid or a part of the actions, and the term means compounds that have at least one retinoid-like action, for example, one or more of cell differentiating action, cell proliferation promoting action, life supporting action, and the like. Whether a certain compound is a retinoid or not can be readily determined by the method described in H. de The, A. Dejean, "Retinoids: 10 years on.", Basel, Karger, 1991, pp. 2-9.

Further, while retinoids generally have a property of binding to a retinoic acid receptor (RAR), and sometimes have property of binding to RXR together with RAR, the retinoid used as the active ingredient of the medicament of the present invention is preferably a retinoid that binds to the subtype a of RAR(RARα) to exhibit an agonist action. Whether a certain compound is an agonist of RARα or not, also including as for a binding to a retinoic acid receptor subtype, can be readily determined by the method of the aforementioned publication.

As the active ingredient of the medicament of the present invention, any of natural retinoids or non-natural retinoids may be used. Preferably, non-natural retinoid may be used. As the non-natural retinoids, those having a basic skeleton comprising an aromatic ring bound with an aromatic carboxylic acid or tropolone by means of a bridging group may be used.

More specifically, as non-natural retinoids, those represented by the following general formula: B-X-A (wherein B represents an aromatic group which may be substituted, X represents a bridging group, and A represents a carboxylic acid-substituted aromatic group or tropolonyl group) can be used.

As the aromatic group represented by B, a phenyl group which may have a substituent is preferred. Type, number, and substituting position of the substituent on the phenyl group are not particularly limited. As the substituent on the phenyl group, for example, a lower alkyl group can be used (in the specification, the term "lower" means a carbon number of 1 to about 6, preferably 1 to 4). As the lower alkyl group, an alkyl group having a linear or branched chain is preferred, and more specific examples include methyl group, ethyl group, n-propyl group, isopropyl group, n-butyl group, sec-butyl group, tert-butyl group, and the like. Other examples of the substituent on the phenyl group include, for example, a lower alkoxyl group such as methoxy group, a halogen atom (the halogen atom may be any of fluorine atom, chlorine atom, bromine atom, and iodine atom), a lower alkyl-substituted silyl group such as trimethylsilyl group, and the like. As the phenyl group, for example, a phenyl group substituted with 2 to 4 of lower alkyl groups, a phenyl group substituted with 1 or 2 of tri(lower alkyl)silyl group, and the like are preferred, and a phenyl group substituted with 2 to 4 of lower alkyl groups, a phenyl group substituted with 2 of tri(lower alkyl)silyl groups, and the like are more preferred.

When two of the lower alkyl groups substituting on the phenyl group are adjacent to each other, they may combine together to form one or two, preferably one of 5- or 6-membered ring together with the ring-constituting carbon atoms of the phenyl group to which they bind. The ring formed as described above may be saturated or unsaturated, and one or more lower alkyl groups such as methyl group and ethyl group may substitute on the ring. On the aforementioned formed ring, preferably 2 to 4 of methyl groups, more preferably 4 of methyl groups, may substitute. For example, it is preferred that two adjacent lower alkyl groups which substitute on the phenyl ring combine together to form 5,6,7,8-tetrahydronaphthalene ring, 5,5,8,8-tetramethyl-5,6,7,8-tetrahydronaphthalene ring, or the like. As the aromatic group represented by B, an aromatic heterocyclic group may also be used. Examples of such retinoid include a retinoid wherein B is a benzofuranyl group which may have a substituent, preferably benzofuran-2-yl group, particularly preferably 4,7-dimethylbenzofuran-2-yl group.

As the carboxylic acid-substituted aromatic group represented by A, a carboxylic acid-substituted phenyl group, a carboxylic acid-substituted heterocyclic group, and the like can be used, and 4-carboxyphenyl group is preferred. Examples of the heterocyclic carboxylic acid constituting the carboxylic acid-substituted heterocyclic group represented by A include, for example, pyrimidine-5-carboxylic acid, and the like. As the tropolonyl group represented by A, tropolon-5-yl group is preferred. On the ring of the carboxylic acid-substituted aromatic group or tropolonyl group, one or more substituents may exist.

Type of the bridging group represented by X is not particularly limited, and examples include, for example, —NHCO—, —CONH—, —N(R$^A$)— (R$^A$ represents a lower alkyl group, for example, cyclopropylmethyl group and the like), —C(R$^B$)(R$^C$)— (R$^B$ and R$^C$ independently represent hydrogen atom, a lower alkyl group, and the like). Further, X may be a divalent aromatic group. For example, X may be pyrrol-diyl group, or the like. Furthermore, the bridging group represented by X and the aromatic group represented by B may combine together to form a ring structure. For example, the basic skeleton of the retinoid represented by B-X-A may be dibenzo[b,f][1,4]thiazepinylbenzoic acid or dibenzo[b,f][1,4]diazepinylbenzoic acid. In the specification, the term "basic skeleton" means a main chemical structure for one or more arbitrary substituents to bind thereto.

As preferred retinoids, all-trans retinoic acid as natural retinoic acid and non-natural retinoid, for example, retinoids comprising a phenyl-substituted carbamoylbenzoic acid or a phenyl-substituted carboxamidobenzoic acid as a basic skeleton can be used. Various retinoids comprising a phenyl-substituted carbamoylbenzoic acid or a phenyl-substituted carboxamidobenzoic acid as a basic skeleton are known. Typical examples of retinoids having a phenyl-substituted carbamoylbenzoic acid as a basic skeleton include Am80 (4-[(5,6,7,8-tetrahydro-5,5,8,8-tetramethyl-2-naphthalenyl) carbamoyl]benzoic acid (refer to Hashimoto, Y., Cell Struct. Funct., 16, pp. 113-123, 1991; Hashimoto, Y., et al., Biochem. Biophys. Res. Commun., 166, pp. 1300-1307, 1990), and typical examples of retinoids having a phenyl-substituted carboxamidobenzoic acid include Tac101 (4-[(3,5-bis-trimethylsilylphenyl)carboxamido]benzoic acid (J. Med. Chem., 33, pp. 1430-1437, 1990).

Preferred retinoids include, for example, compounds represented by the following general formula (I):

[Formula 1]

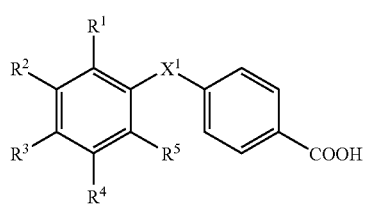

wherein R$^1$, R$^2$, R$^3$, R$^4$, and R$^5$ independently represent hydrogen atom, a lower alkyl group, or a lower alkyl-substituted silyl group, when two of adjacent groups among R$^1$, R$^2$, R$^3$, R$^4$, and R$^5$ are lower alkyl groups, they may combine together to form a 5- or 6-membered ring together with the carbon atoms of the benzene ring to which they bind (this ring may have one or more alkyl groups), and X$^1$ represents —CONH— or —NHCO—.

In the aforementioned general formula (I), as the lower alkyl group represented by R$^1$, R$^2$, R$^3$, R$^4$, and R$^5$, a linear or branched alkyl group having 1 to about 6 carbon atoms, preferably 1 to 4 carbon atoms, can be used. For example, methyl group, ethyl group, n-propyl group, isopropyl group, n-butyl group, sec-butyl group, tert-butyl group, and the like can be used. On the aforementioned lower alkyl group, one or more arbitrary substituents may exist. Examples of the substituents include, for example, hydroxyl group, a lower alkoxyl group, a halogen atom, and the like. Examples of the lower alkyl-substituted silyl group represented by R$^1$, R$^2$, R$^3$, R$^4$, and R$^5$ include, for example, trimethylsilyl group, and the like.

Two of adjacent lower alkyl groups selected from the group consisting of R$^1$, R$^2$, R$^3$, R$^4$, and R$^5$ may combine together to form one or two, preferably one of 5- or 6-membered ring together with the carbon atoms of the benzene ring to which they bind. The ring formed as described above may be saturated or unsaturated, or an aromatic ring, and one or more lower alkyl groups such as methyl group and ethyl group may substitute on the ring. As the alkyl group which may substitute on the ring, a linear or branched alkyl group having 1 to about 6 carbon atoms, preferably 1 to 4 carbon atoms, can be used. For example, methyl group, ethyl group, and the like can be used, and preferably 2 to 4 of methyl groups, more preferably 4 of methyl groups, may substitute. For example, it is preferred that 5,6,7,8-tetrahydronaphthalene ring, 5,5,8,8-tetramethyl-5,6,7,8-tetrahydronaphthalene ring, or the like is formed by the benzene ring on which R$^2$ and R$^3$ substitute, and R$^2$ and R$^3$.

Examples of other preferred retinoids include, for example, retinoids comprising dibenzo[b,f][1,4]thiazepinylbenzoic acid or dibenzo[b,f][1,4]-diazepinylbenzoic acid as the basic skeleton represented by B-X-A. Examples of such retinoids are described in, for example, Japanese Patent Unexamined Publication (KOKAI) No. 10-59951. Particularly preferred examples of such retinoids include, for example, HX630 (4-[2,3-(2,5-dimethyl-2,5-hexano)dibenzo[b,f][1,4]-thiazepin-11-yl]benzoic acid). Further, examples of retinoids wherein X is —N($R^4$)—, and B is an aromatic heterocyclic carboxylic acid include, for example, 2-[2-(N-5,6,7,8-tetrahydro-5,5,8,8-tetramethyl-2-naphthalenyl-N-cyclopropylmethyl)a mino]pyrimidine-5-carboxylic acid. Further, examples of retinoids wherein X is a divalent aromatic group include, for example, 4-[5-(4,7-dimethylbenzofuran-2-yl)-pyrrol-2-yl]benzoic acid. Examples of the compound wherein A is a tropolonyl group include, for example, 5-[[5,6,7,8-tetrahydro-5,5,8,8-tetramethyl-2-naphthalenyl]-carboxamido]tropolone, and the like.

Examples of most preferred retinoids include Am80 (4-[(5,6,7,8-tetrahydro-5,5,8,8-tetramethyl-2-naphthalenyl)carbamoyl]benzoic acid) and Am580 (4-[(5,6,7,8-tetrahydro-5,5,8,8-tetramethyl-2-naphthalenyl)carboxamide]benzoic acid).

As the active ingredient of the medicament of the present invention, salts of the above retinoids may be used. For example, physiologically acceptable salts including metal salts such as sodium salts, potassium salts, magnesium salts, and calcium salts, ammonium salts, organic amine salts such as triethylamine salts, and ethanolamine salts, and the like can be used as the active ingredient of the medicament of the present invention. As the active ingredient of the medicament of the present invention, a prodrug of the above retinoid may be used. The term "prodrug" means a compound or a salt thereof which is, after oral or parenteral administration to an mammal, subjected to a structural change such as hydrolysis in vivo, preferably in blood, to produce the above retinoid or a salt thereof. For example, various means for producing prodrugs from pharmaceutical compounds having carboxylic acid, amino group, hydroxyl group or the like are known, and one of ordinary skill in the art can choose appropriate means. Types of the prodrug of the retinoid or a salt thereof are not particularly limited. For example, where a retinoid has carboxylic acid, an example includes a prodrug wherein the carboxylic acid is converted into an alkoxycarbonyl group. Preferred examples include ester compounds such as methoxycarbonyl group or ethoxycarbonyl group.

The aforementioned retinoid may have one or more asymmetric carbons depending on the types of substituents, and any optical isomers based on these asymmetric carbons, any mixtures of optical isomers, racemates, diastereoisomers based on two or more asymmetric carbons, any mixtures of diastereoisomers, and the like can be used as the active ingredient of the medicament of the present invention. Furthermore, geometrical isomers based on cis- or trans-configuration of double bond, any mixtures of geometrical isomers, and any hydrates or solvates of the compounds in free forms or in the form of a salt can also be used as the active ingredient of the medicament of the present invention.

The medicament of the present invention can be used for preventive and/or therapeutic treatment of a lower urinary tract symptom caused by a lower urinary tract disorder. In the specification, the term "lower urinary tract disorder" encompasses disorders relating to functions of lower urinary tract, specifically, disorders of miction. The term "lower urinary tract" means the whole of the urinary tract, except kidney, that functions to storage and periodically void urine, generally including ureter, urinary bladder, sphincter muscle, prostate gland, and urethra. The term "preventive and/or therapeutic treatment of a lower urinary tract symptom" encompasses wide variety of idea such as amelioration or elimination of a symptom, prevention of aggravation or occurrence of a symptom or the like. This term should not be limitatively construed in any sense and should be construed with broadest meanings.

Examples of the lower urinary tract symptoms caused by the lower urinary tract disorders include, for example, main symptoms such as storage symptoms, voiding symptoms, and post micturition symptoms, and also include urinary tract pain such as painful urination, bladder pain, suprapubic pain, and urethral pain, detrusor overactivity, bladder discomfort, lower urinary tract discomfort, and voiding difficulty. The term also encompasses blood in the urine accompanied by lower urinary tract disorders. The storage symptoms include pollakisuria, urinary urgency, urinary incontinence, enuresis, abnormal bladder sensation, bladder pain during the urinary storage, and bladder discomfort during the urinary storage. The voiding symptoms include slow stream, splitting of the urine stream, spraying of the urine stream, intermittent stream, hesitancy, straining to void, and terminal dribble. The post micturition symptoms include feeling of incomplete emptying, and post micturition dribble. The medicament of the present invention can reduce or eliminate one or more symptoms among the aforementioned lower urinary tract symptoms resulting from the lower urinary tract disorders. Among them, lower urinary tract symptoms such as pollakisuria, urinary urgency, urinary incontinence, enuresis, abnormal bladder sensation, painful urination, bladder pain, suprapubic pain, blood in the urine, bladder discomfort, bladder pain during urinary storage, or bladder discomfort during urinary storage are preferred objects to be preventively and/or therapeutically applied by the medicament of the present invention.

Examples of the lower urinary tract disorders which cause the lower urinary tract symptoms include, for example, diseases of prostate such as hyperplasia of prostate, prostatitis, prostatodynia, prostatocystitis, abscess of prostate, congestion of prostate, haemorrhage of prostate, or atrophy of prostate, diseases of urethra such as urethritis, urethral abscess, urethral stricture such as post-traumatic urethral stricture and postinfective urethral stricture, urethral fistula, urethral diverticulum, or urethral caruncle, diseases or lesions of bladder such as bladder neck sclerosis, bladder neck obstruction, vesicointestinal fistula, diverticulum of bladder, bladder cancer, overactive bladder, acute cystitis, chronic cystitis, interstitial cystitis, trigonitis, irradiation cystitis, cystitis from cancer chemotherapy agents, tuberculous cystitis, interstitial cystitis, or painful bladder syndrome. In the present specification, "pathology of the bladder" includes desquamation of bladder epithelium, fibrosis, injury, redness, bleeding, edema, ulcer, hemorrhagic granulation, tumor or inflammation in the muscle layer, the interstitial layer, the mucosal layer, or serosa of the bladder wall. The medicament of the present invention can exert high effectiveness in reducing or eliminating lower urinary tract symptoms caused by interstitial cystitis, or painful bladder syndrome.

Hyperplasia of prostate is a disease in which the prostate gland becomes enlarged by expanding prostatic adenoma in the prostate gland, and it occurs mainly as a result of aging. Hyperplasia of prostate is a common benign disease, but when prostatic enlargement proceeds, symptoms such as pollakisuria, urinary urgency, or urinary incontinence occur. When the urinary tract is further obstructed, voiding dysfunction such as intermittent stream or feeling of incomplete emptying or in some cases renal dysfunction occurs. Prostatitis refers to an inflammatory condition of the prostate gland, and it is roughly categorized into acute prostatitis and chronic prostatitis. In most cases, acute prostatitis is caused by bacterial infection of the prostate gland. Pathogenic bacteria of the disease are mainly gram-negative rod bacteria including *Escherichia Coli*. Acute prostatitis causes symptoms such as fever, voiding difficulty, feeling of incomplete emptying, pollakisuria, or painful urination. Chronic prostatitis is roughly categorized into chronic bacterial prostatitis and chronic non-bacterial prostatitis. While chronic bacterial prostatitis in which infection of bacteria becomes chronic mostly shifts from acute bacterial prostatitis, chronic non-bacterial prostatitis is characterized by chronic inflammation of prostate not accompanied by bacterial infection. Symptoms of chronic prostatitis include pollakisuria, feeling of incomplete emptying, perineal discomfort and pain, and voiding difficulty. Prostatodynia causes symptoms similar to prostatitis in spite of no objective findings of prostate inflammation. Prostatodynia is also called as prostatic pain.

Bladder neck sclerosis is a disease which causes voiding dysfunction by hardening of the bladder wall at the bladder neck. The detailed cause of the disease has not yet been elucidated. Symptoms of the disease are similar to symptoms of huperplasia of prostate, such as pollakisuria and feeling of incomplete emptying.

Interstitial cystitis is a disease whose symptoms include pollakisuria, increased desire to urinate, urinary urgency, and bladder pain, in the absence of urinary tract infection or other obvious pathology. Typical interstitial cystitis is characterized by the presence of Hunner's ulcer or glomerulation on cystoscopy, but there are some interstitial cystitis patients without Hunner's ulcer or glomerulation. The diagnostic criteria for interstitial cystitis have been proposed as NIDDK (National Institute of Diabetes and Digestive and Kidney Diseases) criteria or ICDB (Interstitial Cystitis Data Base) criteria.

Painful bladder syndrome is usually used as a synonym of interstitial cystitis. According to the ICS (International Continence Society) definition, painful bladder syndrome is a disease which has a suprapubic pain related to bladder filling, accompanied by other symptoms such as increased daytime and nighttime frequency, in the absence of urinary tract infection or other obvious pathology.

Overactive bladder is a syndrome whose main symptom is urinary urgency. The main complaint of the disease is urinary urgency usually accompanied by pollakisuria or nocturia, sometimes accompanied by urge urinary incontinence. Detrusor overactivity is considered to be the main cause of the disease. When there is infection or other obvious pathology, it is distinguished from overactive bladder. Overactive bladder includes neurogenic bladder caused by spinal cord diseases or neurological disorders, and non-neurogenic bladder.

The medicament of the present invention comprises, as an active ingredient, one or two or more substances selected from the group consisting of the aforementioned retinoid and a salt thereof, and a hydrate thereof and a solvate thereof. A preferred effectiveness may sometimes be obtained by administration of two or more different retinoids in combination. As the medicament of the present invention, the aforementioned substance, per se, may be administered. Preferably, the medicament can be administered as a pharmaceutical composition for oral or parenteral administration which can be prepared by a method well known to one of ordinary skill in the art.

As pharmaceutical compositions suitable for oral administration, examples include tablets, capsules, subtilized granules, granules, liquids, and syrups. As pharmaceutical compositions suitable for parenteral administration, examples include injections, suppositories, inhalant, eye drops, nasal drops, ointments, creams, and plasters. Two or more pharmaceutical compositions may be used in combination. Preferred forms of the medicament of the present invention include pharmaceutical compositions for oral administration.

For example, for preparation of pharmaceutical compositions for oral administration such as tablets, capsules, granules, and powders, excipients such as lactose, crystalline cellulose, and starch, lubricants such as magnesium stearate and talc, binders such as hydroxypropylcellulose and polyvinylpyrrolidone, disintegrators such as carboxymethylcellulose calcium and low substituted hydroxypropyl methylcellulose, coating agents such as hydroxypropylmethylcellulose, macrogol, and silicone resin, and the like may be used as required. For preparation of eye drops, isotonic agents such as sodium chloride, potassium chloride, or concentrated glycerin, buffering agents such as sodium phosphate, sodium acetate, boric acid, or monoethanol amine, stabilizing agents such as sodium citrate or edetate sodium, antiseptics such as benzalkonium chloride and a paraoxybenzoic acid, surface active agents such as polysorbate 80 and polyoxyethylene hydrogenated castor oil, pH adjusting agents such as diluted hydrochloric acid or sodium hydroxide and the like may be used as required. A pH of the eye drop is not particularly limited. A range of 4 to 8 is preferred which is acceptable for phthalic preparations.

A dose of the medicament of the present invention is not particularly limited. The dose may be suitably chosen depending on symptoms, age, body weight and the like of a patient, a method for administration, a type of active ingredient and the like. For example, for oral administrations, a dose of 0.01 to 1,000 mg, preferably 0.1 to 10 mg per day may be administered once or several times as divided portions. However, the aforementioned doses are only for examples, and the dose may be appropriately increased or decreased.

EXAMPLE

The present invention will be explained more specifically with reference to the example. However, the scope of the present invention is not limited to the following example.

Example 1

Evaluation in a Rat Hydrochloric Acid-induced Cystitis Model

On day 1, Crlj:CD(SD) male rats at 8 weeks of age were anesthetized by 2% isofurane inhalation and the abdomen of the rats were opened. After cannula was inserted into the bladder and fixed, the incision was closed with suture. On day 2, 0.2 N hydrochloric acid was injected into the bladder through cannula for 15 min to induce cystitis. On day 3, the first oral administration of a drug was performed. Since then, the drug was administrated once a day continuously for 7 days. As a retinoid drug, 3 mg/kg tamibarotene (Am80, 4-[(5,6,7,8-tetrahydro-5,5,8,8-tetramethyl-2-naphthalenyl)-carbamoyl] benzoic acid) suspended in 0.5% carboxymethylcellulose was orally administered. For the control group, 0.5% carboxymethylcellulose was orally administered. On day 10, bladder function under unanesthetized and unrestrained state was evaluated by cystometry. Via a three-way stopcock, warm saline (37° C.) was infused into the tube which was inserted into the bladder. At the other end of a three-way stopcock, bladder pressure was measured for 60 min by a pressure amplifier through a pressure transducer. At the same time, the weight change of excreted urine was measured using a balance. From these measured data, basal bladder pressure, maximum bladder pressure, micturition interval, and micturition volume were calculated. 5 rats were used in each group, control and tamibarotene group.

The results are shown in Table 1. Values were indicated as average ±standard error. The difference between averages of control group and tamibarotene group was evaluated by Student's t-test (***p<0.001 compared with control). It was revealed that micturition interval was significantly improved in 3 mg/kg tamibarotene-administered group compared to control group. These results suggested that the medicament of the present invention has an effect of improving storage symptoms, and therefore, it was concluded that the medicament of the present invention has effectiveness on prevention and/or treatment of lower urinary tract symptoms.

TABLE 1

|  | Basal bladder pressure (mmHg) | Maximum bladder pressure (mmHg) | Micturition interval (second) | Micturition volume (g) |
| --- | --- | --- | --- | --- |
| Control group | 17.1 ± 1.9 | 37.7 ± 3.6 | 306 ± 13 | 0.26 ± 0.04 |
| Tamibarotene-administered Group | 15.1 ± 2.8 | 36.6 ± 6.0 | 884 ± 113*** | 0.61 ± 0.24 |

What is claimed is:

1. A method for therapeutic treatment of a lower urinary tract symptom selected from the group consisting of pollakisuria, urinary urgency, bladder discomfort, bladder pain during urinary storage, and bladder discomfort during urinary storage caused by a lower urinary tract disorder selected from a lesion of bladder or an overactive bladder, which comprises administering a therapeutically effective amount of Am80 (4-[(5,6,7,8-tetrahydro-5,5,8,8-tetramethyl-2-naphthalenyl) carbamoyl]benzoic acid) to a mammal in need of treatment of the lower urinary tract symptom.

2. The method according to claim 1, wherein the mammal is a human.

* * * * *